(12) United States Patent
McCauley et al.

(10) Patent No.: US 9,632,064 B2
(45) Date of Patent: Apr. 25, 2017

(54) GAS CHROMATOGRAPH SYSTEM EMPLOYING HYDROGEN CARRIER GAS

(71) Applicant: Thermo Finnigan LLC, San Jose, CA (US)

(72) Inventors: Edward B. McCauley, Cedar Park, TX (US); Franco Ponciroli, Rodano (IT); Paolo Magni, Rodano (IT)

(73) Assignee: Thermo Finnigan LLC, San Jose, CA (US)

( * ) Notice: Subject to any disclaimer, the term of this patent is extended or adjusted under 35 U.S.C. 154(b) by 135 days.

(21) Appl. No.: 14/334,282

(22) Filed: Jul. 17, 2014

(65) Prior Publication Data

US 2015/0330953 A1 Nov. 19, 2015

(30) Foreign Application Priority Data

May 13, 2014 (EP) ..................... 14425056

(51) Int. Cl.
*G01N 1/00* (2006.01)
*G01N 30/20* (2006.01)
(Continued)

(52) U.S. Cl.
CPC ........... *G01N 30/20* (2013.01); *B01D 53/025* (2013.01); *G01N 30/16* (2013.01); *G01N 30/34* (2013.01);
(Continued)

(58) Field of Classification Search
CPC .. G01N 30/88; G01N 2030/025; G01N 30/74; G01N 2030/8854; G01N 30/02; G01N 30/20
(Continued)

(56) References Cited

U.S. PATENT DOCUMENTS 3,077,766 A   2/1963 Reinecke
3,858,435 A * 1/1975 Stevens ................. G01N 30/28
                                                    422/89
(Continued)

FOREIGN PATENT DOCUMENTS

GB        2485065 A       2/2012
WO    WO 97/14957 A1     4/1997
WO    WO 98/36815 A1     8/1998

OTHER PUBLICATIONS

Harry Prest, "Reducing Helium Costs more than 10-fold with the PCT Gas Saver mode," Agilent Technologies, 2010, 5990-5444EN, pp. 1-10, https://www.chem.agilent.com/Library/technicaloverviews/Public/5990-5444EN.pdf.

*Primary Examiner* — Eric S McCall
*Assistant Examiner* — Mohammed E Keramet-Amircolai
(74) *Attorney, Agent, or Firm* — Thomas F. Cooney (57) ABSTRACT

An injection port for a gas chromatograph (GC) is operated such that, during an injection sequence, an inert gas is used for sample transfer to the analytical column while hydrogen is subsequently utilized for the majority of the analytical separation. This allows for a high degree of chromatographic efficiency, while also reducing unwanted chemical reactions involving hydrogen and/or reactive solvents in a hot injection port. Certain embodiments also provide an increased margin of safety when using hydrogen, since the total flow may be limited such that the concentration of hydrogen in the GC oven never exceeds a safety limit, such as the lower explosive limit.

13 Claims, 5 Drawing Sheets

(51) Int. Cl.
  *G01N 30/16* (2006.01)
  *G01N 30/34* (2006.01)
  *B01D 53/02* (2006.01)
  *G01N 30/02* (2006.01)
  *B01D 15/14* (2006.01)

(52) U.S. Cl.
  CPC ........ *B01D 15/14* (2013.01); *G01N 2030/025* (2013.01)

(58) Field of Classification Search
  USPC .................. 73/1.43, 19.02, 23.22, 23.35
  See application file for complete search history.

(56) References Cited

U.S. PATENT DOCUMENTS

| | | | |
|---|---|---|---|
| 4,230,464 A | 10/1980 | Bonmati et al. | |
| 4,935,040 A * | 6/1990 | Goedert | G01N 30/20 210/198.3 |
| 5,183,072 A | 2/1993 | Pengler | |
| 5,611,846 A | 3/1997 | Overton et al. | |
| 6,063,166 A | 5/2000 | Wilson | |
| 6,074,461 A | 6/2000 | Wilson | |
| 6,293,995 B2 | 9/2001 | Wilson | |
| 6,641,783 B1 * | 11/2003 | Pidgeon | G01N 30/20 210/656 |
| 7,384,453 B2 | 6/2008 | Bostrom et al. | |
| 8,308,854 B2 | 11/2012 | McCauley et al. | |
| 8,371,152 B2 | 2/2013 | McCauley et al. | |
| 8,776,576 B2 * | 7/2014 | Okada | G01N 30/28 73/23.35 |
| 2003/0100124 A1 * | 5/2003 | Beens | G01N 30/465 436/161 |
| 2006/0144237 A1 * | 7/2006 | Liang | G01N 30/6095 96/101 |
| 2007/0125233 A1 | 6/2007 | Bostrom et al. | |
| 2009/0272270 A1 * | 11/2009 | McGill | B01J 20/205 96/101 |
| 2009/0321356 A1 * | 12/2009 | Gerhardt | G01N 30/6095 210/656 |
| 2013/0025347 A1 * | 1/2013 | Rhodes | G01N 30/88 73/23.39 |

\* cited by examiner

GAS CHROMATOGRAPH SYSTEM EMPLOYING HYDROGEN CARRIER GAS

CROSS REFERENCE TO RELATED APPLICATION

This application claims, under 35 U.S.C. §119(a), the benefit of the filing date and the right of priority to European application EP 14425056, filed on May 13, 2014.

FIELD OF THE INVENTION

This invention relates to gas chromatography and, more particularly, to improved performance and safety when utilizing hydrogen in gas chromatograph injectors and columns.

BACKGROUND OF THE INVENTION

Gas chromatographs are well known devices used to separate chemical mixtures. Within a gas chromatograph is an analytical column which generally comprises an elongate fused silica capillary tube coated internally with a cross bonded stationary phase. The column may be from a few tens to a few hundreds of micrometers in diameter and vary in length from a few meters to as many as a hundred meters or so. It is known to use a carrier gas in these columns such as helium, nitrogen, argon or hydrogen in order to allow transport of the separated analytes through the column and to a suitable detection system. The various gasses used as the carrier gas have differing viscosities, heat conductivities, diffusion rates and chemical activities amongst other properties.

Figure 1:
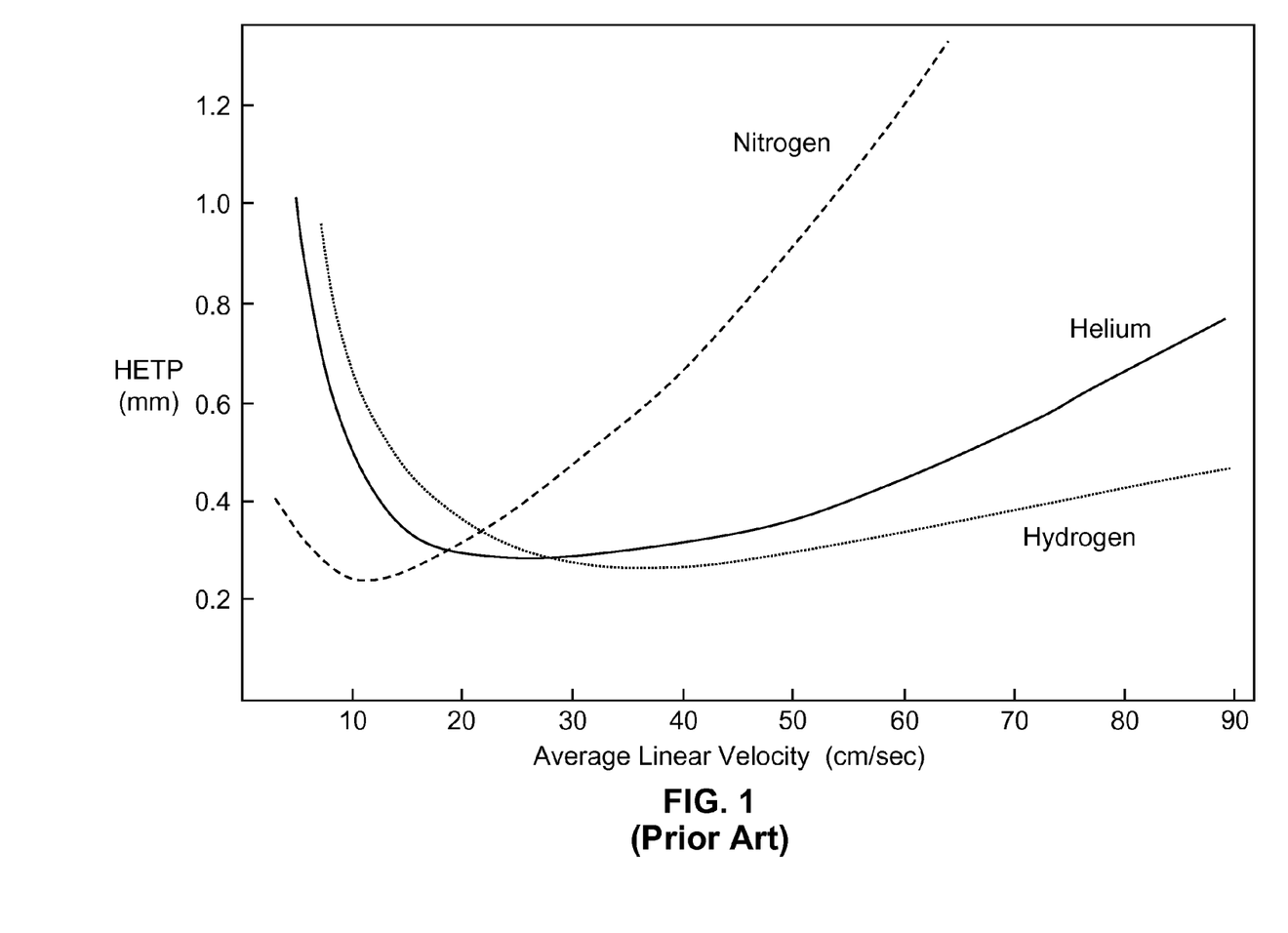
FIG. 1 is a Van Deemter plot showing the chromatographic separation efficiency versus linear flow velocity for three different gas chromatograph carrier gas types.

FIG. 1 illustrates the well known Van Deemter plot showing the optimum linear velocity for various carrier gas types. As can be seen in the plot, nitrogen offers very good separation efficiency (a low value of Height Equivalent of a Theoretical Plate or HETP) at low linear velocities, but this efficiency rapidly drops as the linear velocity increases. By contrast, hydrogen can be utilized at high linear velocities without much increase in the height equivalent of a theoretical plate. For this reason, hydrogen may be used in order to achieve the best separation per unit time.

Unfortunately, while hydrogen can achieve high levels of separation power per unit time, it has the disadvantage of being more chemically reactive than nitrogen, helium or argon. It has been observed that hydrogen can be chemically reactive toward unsaturated analytes, forming compounds not present in the original sample. For example, it is known that styrene can be converted to ethyl benzene in a hot injection port in the presence of hydrogen. Additionally, the amount of conversion can vary depending on the activity of the injection port liner, rendering quantitation which is non-reproducible. It is also known that certain solvents e.g. methylene chloride can form hydrochloric acid at elevated temperatures in the presence of hydrogen. This can have a detrimental effect on the column stationary phase chemistry. The acidity as well as the polarity of the hydrochloric acid can also give non-linearity in the response factors for certain classes of compounds.

Adverse hydrogen reactivity may also be observed within an injector which is initially cool then subsequently heated rapidly such as occurs within a PTV (programmed temperature vaporization) injector. In addition to being potentially reactive toward chemical analytes of interest, the explosive nature of hydrogen is well known, and precautions need to be taken in order to prevent an unwanted explosion. These precautions may include a costly hydrogen sensor capable of disabling power to the system in the event of a large hydrogen leak.

Generally, injection ports for capillary columns control flow through the capillary column indirectly by applying pressure in accordance with the Poiseuille equation:

$$\frac{dV}{dt} = \frac{\pi r^4}{16\eta L}\left(\frac{p_i^2 - p_0^2}{p_0}\right) \qquad \text{Eq. 1}$$

in which V(t) is the volume of gas transferred as a function of time, t, $p_i$ is inlet pressure, $p_o$ is outlet pressure, L is the length of the column, $\eta$ is the viscosity of the gas and r is the column internal radius. The indirect control of flow using pressure in order to achieve a calculated flow is achieved by an Electronic Pressure Control (EPC) unit. It should be noted that, in this document, a distinction is made between a "transfer gas" that is used to transfer volatilized sample from a GC sample injector into a GC analytical column and a "carrier gas" which is used to: (i) facilitate separation of sample components as they differentially partition between the gas and the column stationary phase and travel through the length of the GC analytical column under the carrier gas flow and (ii) transport the separated gas components from an exit end of the GC analytical column to a detector for analysis.

Figure 2:
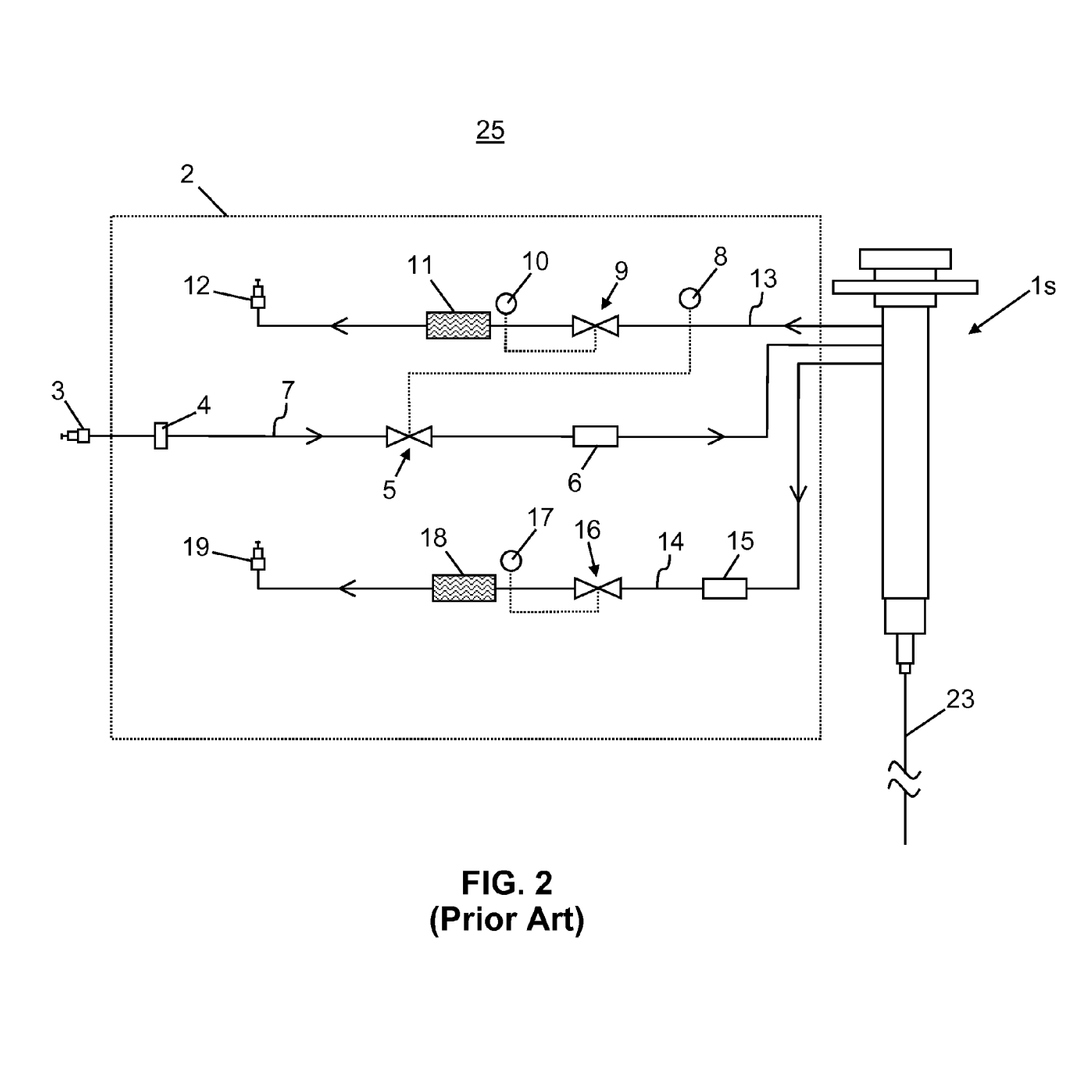
FIG. 2 is a schematic diagram of a conventional gas supply and exhaust system for a gas chromatograph comprising a split/splitless injector and an electronic pressure controller.

FIG. 2 illustrates a conventional gas supply and exhaust system 25 that comprises an Electronic Pressure Control unit 2 interfaced to a split/splitless injector 1s. In addition to the pneumatic control elements of the EPC 2 illustrated in the accompanying drawings, the EPC 2 also comprises an electronic controller (not illustrated) such as a circuit board that is electronically coupled to the illustrated pneumatic elements and that comprises program logic that includes instructions that cause the various valves to operate and that reads the various pressure sensors. The split/splitless (SSL) injector 1s is provided for receiving injections of liquid samples from a syringe (not illustrated), for flash vaporizing the liquid samples by application of heat, for mixing the volatilized sample material with a transfer gas or carrier gas and for providing a portion of the volatilized sample material to a GC analytical column 23.

The injector temperature is typically maintained (in the case of an SSL) or rapidly heated (in the case of a PTV) to a temperature in the range of 150° C. to 450° C. during sample transfer. By contrast, the analytical column is maintained at a much lower temperature during this time— typically in the range of 40° C. to 100° C. The temperature control mechanisms of the injector and the oven are independent of one another. Transfer of volatilized sample components into the cooler GC analytical column causes these components to condense on or to be deposited in or on the stationary phase within a narrow band at the inlet end of the column. Flow of the carrier gas through the GC analytical column causes differential partitioning of the various components between the stationary phase and the gaseous mobile phase and facilitates transport of the so-separated components through the column towards its outlet end. Generally, the analytical column is housed within an oven (not shown) that is configured so as to heat air within the oven to a controlled temperature and to circulate the heated air around the column so as to provide a uniform controlled temperature along the entire length of the column.

Pneumatic control elements of the EPC such as pressure sensors, proportional valves and fixed restrictors are used to carry out the functions of gas delivery and flow control for various functions such as column pressurization, septum purge and split flow control. The carrier gas supply, e.g. helium, is introduced under pressure into a gas inlet line 7 by means of a gas fitting 3. A controlled pressure of the carrier gas is provided to the injector by the electronic pressure controller 2 which results in a controlled flow of carrier gas through column 23. A fine porosity filter 4, e.g. a stainless steel frit, removes any particulate matter that may foul operation of a proportional valve 5 that is disposed downstream in the gas inlet line 7. The proportional valve 5 maintains a setpoint pressure within the body of the injector 1s in response to measurements provided by pressure sensor 8 in order to establish a calculated flow in the analytical column 23 in accordance with the Poiseuille equation. The pressure sensor 8 provides a feedback loop to a control circuit of the electronic pressure controller. Optionally, a chemical trap 6, such as a trap comprising activated charcoal is included in the gas inlet line 7 to scrub the carrier gas of potential contaminants, e.g. hydrocarbons and/or oxygen.

As is known, generally only a portion (and, frequently, only a small portion) of the volatilized sample material and carrier gas flow actually enters the column 23. The remainder of the volatilized sample material and carrier gas flow is exhausted from the system by means of septum purge vent line 13 and, frequently, split flow vent line 14. Flow restrictor 11 and flow restrictor 18, disposed, respectively, in the septum purge vent line 13 and split flow vent line 14 maintain a pressure difference between the exhaust ports 12, 19, which are at ambient pressure, and the higher-pressure segments of the vent lines 13, 14 that are adjacent to the injector 1s. Pressure sensors 10, 17 measure the pressures of the high-pressure segments of the vent lines 13, 14. This information is provided as continuous feedback to the electronic pressure controller which calculates the pressure differences across the flow restrictors 11, 18 and operates the proportional valves 9, 16 so as to maintain desired flow rates within the vent lines 13, 14, in accordance with a mathematical calculation or calibrated lookup table. A chemical trap 15 may be included in the split flow vent line 14 to protect the proportional valve 16 from contamination by various oils and greases that may volatilize from the sample or outgas from injector components. Another similar chemical trap (not shown) may also be included in the septum purge vent line 13.

The injector 1s includes two basic modes of operation: split and splitless. In the split injection mode, a split flow is established that exits the split vent line 14. This mode of operation is used for injection of concentrated analytes to prevent overloading of the column or saturation of the detection system used at the terminal end of the column. In the splitless mode of operation, the split vent line 14 is closed (i.e., proportional valve 16 is closed) during a sample injection to cause the bulk of the sample material to be transferred to the capillary column. After a specified time interval, the split vent line is once again opened to vent residual solvent vapors and to dilute any contaminants that might outgas from contaminated surfaces.

The indirect control of flow using pressure as described above can result in a relatively unbounded flow of carrier gas if the column should break near the point where the column enters the injector. This presents a potential safety hazard associated with the conventional system 25 if hydrogen is utilized as the carrier gas. Nonetheless, the higher price and sporadic availability of helium have led to an increased market demand for hydrogen in spite the various disadvantages of the latter.

Accordingly, there is a need in the art for a gas chromatograph with a carrier gas system which allows the high separation efficiency per unit time of hydrogen without incurring the negative aspects of chemical reactivity toward analytes in a hot injector or other hot zone of a gas chromatograph. There is also a need for systems and techniques that allow hydrogen to be used as a carrier gas without formation of hydrochloric acid when injecting halogenated solvents. There is a further need to provide a hydrogen-using gas chromatograph system that provides an increased margin of safety over that provided with prior art hydrogen equipped chromatographs. The present invention addresses these needs.

SUMMARY

The inventors have realized that, because an analytical column of a gas chromatograph system is generally maintained at a lower temperature than the temperature of an associated injector, different gas compositions may be advantageously employed at different stages of a gas chromatography procedure. Accordingly, a method of introducing an analyte-bearing sample into an injection port of a gas chromatograph includes a first step wherein an inert gas is used to pressurize the inlet and provide column flow during an injection period, and a second step wherein following the injection and sample transfer period, hydrogen is used as the carrier gas for the analytical separation. The gas employed in the first step is here referred to as a "transfer gas" and may comprise helium, nitrogen or argon or some combination thereof or some other gas that does not react with either the sample or injector components at the relatively higher temperature of the injector. The common designation of "carrier gas" is used herein to describe the gas employed in the second step, which may comprise hydrogen. The present invention thus differs from conventional gas chromatograph systems and gas chromatography methods in that, in accordance with the conventional systems and methods, a single gas type—typically helium—is used as both the transfer gas and the carrier gas.

Accordingly, in a first aspect of the present teachings, a gas chromatography (GC) system is provided, the system comprising: a sample injector comprising a heater and a gas inlet port; a gas inlet line fluidically coupled to the gas inlet line operable to supply gas to the sample injector; a GC analytical column fluidically coupled to the sample injector and configured to receive a volatilized sample and the supplied gas from the sample injector; a source of hydrogen gas and a source of an inert gas; a selection valve fluidically coupled between the gas inlet line and each of the source of hydrogen and the source of inert gas; and an electronic controller electrically coupled to the selection valve and comprising program instructions so as to cause the selection valve to cause the inert gas to be delivered to the sample injector during transport of the volatilized sample from the sample injector to the GC analytical column and to cause the hydrogen gas to be delivered to the sample injector during chromatographic separation of sample components within the GC analytical column. In various embodiments, the source of hydrogen may comprise a hydrogen generator apparatus.

In a second aspect of the present teachings, a gas chromatography (GC) system is provided, the system comprising: a sample injector comprising a heater and a gas inlet port; a gas inlet line fluidically coupled to the gas inlet line operable to supply an inert gas to the sample injector from a source of inert gas; a GC analytical column fluidically coupled to the sample injector and configured to receive a volatilized sample and the supplied gas from the sample injector; a tee coupler fluidically coupled between the sample injector and the GC analytical column; a source of hydrogen gas; a hydrogen supply line fluidically coupled between the tee coupler and the source of hydrogen gas; and a calibrated flow restrictor and a shutoff valve fluidically coupled between a first and a second portion of the hydrogen supply line; wherein the shutoff valve is configured to supply a flow of hydrogen carrier gas from the source of hydrogen gas to the GC analytical column only during chromatographic separation of sample components within the GC analytical column and during transport of the separated components to a detector and the calibrated flow restrictor is configured to limit a flow rate of the hydrogen carrier gas to within a safety limit. In various embodiments, the source of hydrogen may comprise a hydrogen generator apparatus. In various embodiments, the calibrated flow restrictor may be configured to limit the flow rate of the hydrogen carrier gas to less than 5 standard cubic centimeters per minute. In various embodiments, the calibrated flow restrictor may be configured such that the flow of hydrogen carrier gas to the GC analytical column is greater than a flow rate that can be accommodated by the column and such that a portion of the hydrogen carrier gas mixes with a purge gas that flows through the sample injector.

In a third aspect, there is provided a method for operating a gas chromatography (GC) system comprising a sample injector and a GC analytical column, the method comprising: (i) causing an inert transfer gas to flow into the sample injector; (ii) introducing a liquid sample into the sample injector such that components of the sample are volatilized therein and transferred into the GC analytical column under the flow of inert transfer gas; (iii) causing hydrogen carrier gas to flow into the GC analytical column so as to facilitate separation of the transferred sample components within the GC analytical column and so as to transport the separated components to a detector; and (iv) ceasing the flow of hydrogen carrier gas. In various embodiments, the steps (i) through (iv) may be repeated, wherein another liquid sample is introduced into the sample injector during the repeated step (ii). In various embodiments, the step (iii) of causing hydrogen carrier gas to flow into the GC analytical column may comprise causing the hydrogen carrier gas to flow into and through the sample injector into the GC analytical column. In some of such embodiments, the step (iii) may be performed by operation of a gas selection valve that is fluidically coupled between the sample injector and each of an inert gas source and a hydrogen gas source. In various alternative embodiments, the step (iii) of causing hydrogen carrier gas to flow into the GC analytical column may comprise causing the hydrogen carrier gas to flow from a hydrogen gas source into a tee coupler fluidically coupled between the sample injector and the GC analytical column and, additionally, the hydrogen carrier gas may be caused to flow at a flow rate that is greater than a maximum flow rate that can be accommodated by the GC analytical column such that a portion of the hydrogen carrier gas mixes with a purge gas that flows through the sample injector. In some of such embodiments, the method may further comprise: (v) causing a purge gas to flow through the GC analytical column during an idle time when no samples flowing through or are being transferred into the GC analytical column, wherein the purge gas is introduced through the tee coupler.

BRIEF DESCRIPTION OF THE DRAWINGS

The above noted and various other aspects of the present invention will become apparent from the following description which is given by way of example only and with reference to the accompanying drawings, not necessarily drawn to scale, in which.

DETAILED DESCRIPTION

This disclosure describes improved gas chromatograph systems and methods for operating gas chromatograph systems. The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. To more particularly appreciate the features of the present invention, the reader is referred to FIGS. 1 through 5 in conjunction with the following description.

Figure 3:
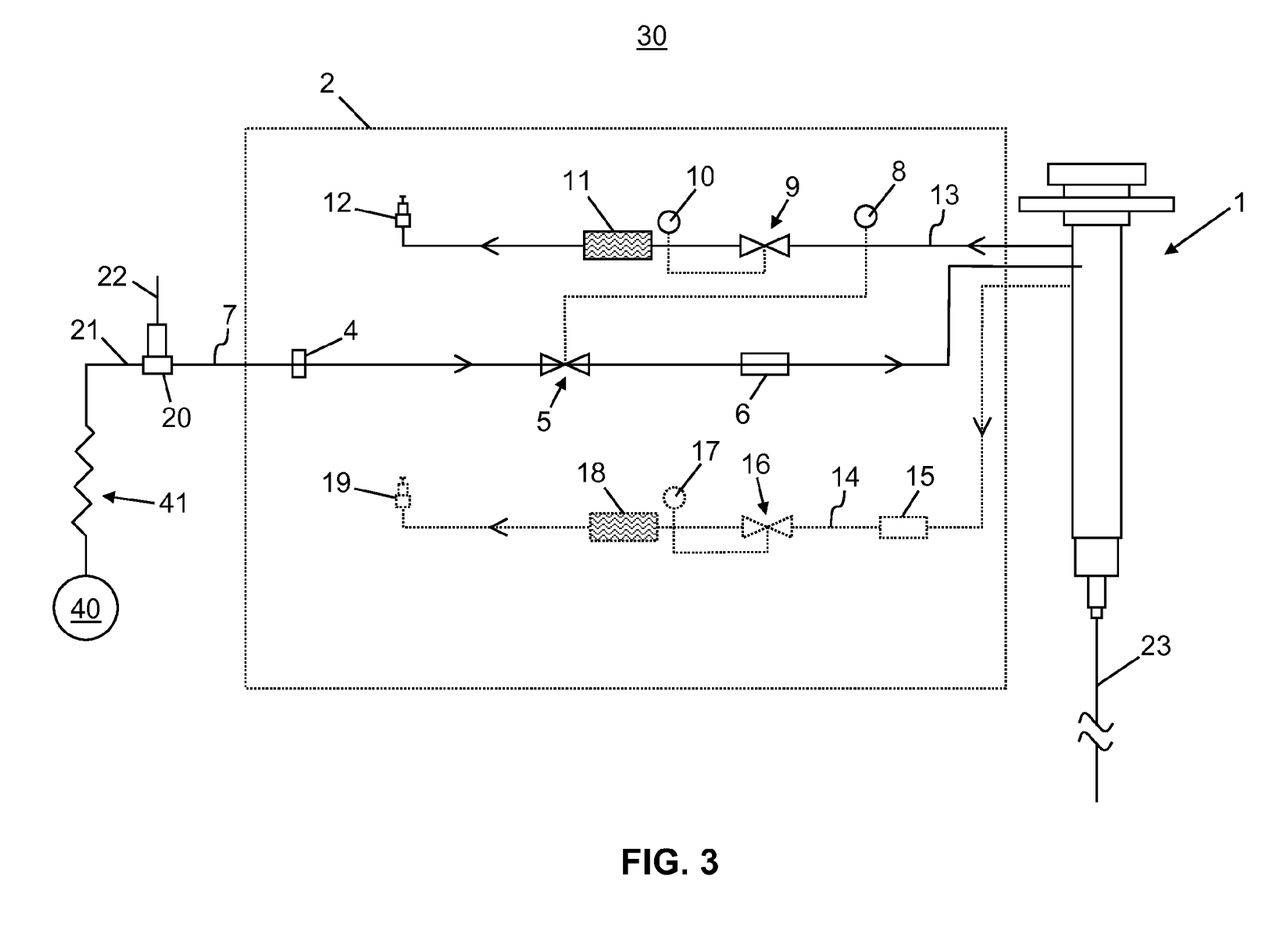
FIG. 3 illustrates a first gas supply and exhaust system for a gas chromatograph in accordance with an embodiment of the present teachings.

FIG. 3 illustrates a first gas supply and exhaust system 30 for a gas chromatograph in accordance the present teachings. The injector 1 of the system 30 may be of either the SSL or PTV type. In FIG. 3, the split flow vent line 14 and its various components (chemical trap 15, proportional valve 16, pressure sensor 17, flow restrictor 18 and exhaust port 19) are illustrated with dotted lines to indicate that they may not be present if split flow is not employed. The EPC unit 2 may be fed hydrogen gas at the gas inlet line 7 from the common port of a three-way valve 20. The three way valve 20 is used to select between hydrogen gas provided by hydrogen source 40 and delivered at a port 21 and an inert gas such as nitrogen, helium or argon delivered at a port 22. In preparation of an injection of a sample into injector 1, the valve 20 is configured to deliver the inert gas, such as nitrogen, helium or argon. Following the injection and sample transfer to an analytical column 23, the three-way valve 20 is configured to deliver hydrogen. In this manner, analytes of the sample which can react with hydrogen in the presence of heat are precluded from doing so, since hydrogen is not present during the initial hot sample transfer. Furthermore, injected solvents which might otherwise react with hydrogen are precluded from doing so, since during the injection sequence a non-hydrogen gas is used. Some sample compounds may still react with hydrogen adversely later within the analytical column in a temperature programmed run, but compounds which elute at earlier times and lower chromatograph temperatures can be prevented from doing so. Optionally, the carrier gas could be switched a second time so as to use the inert gas as the carrier gas (instead of using hydrogen as the carrier gas) during later, high-temperature stages of a temperature programmed run. The changeover from hydrogen to an inert carrier gas may require concurrent adjustment of the gas velocity to a lower value so as to maintain adequate chromatographic separation (see FIG. 1).

An activated charcoal trap 6 for removal of trace impurities may optionally be included in the gas inlet line 7 of the system 30 (FIG. 3). If present, the trap 6 may be provided with a minimum amount of adsorbent in order to provide a minimum in void volume and surface area. Removing or minimizing the size of trap 6 provides the sharpest transition between hydrogen and inert gas. A calibrated flow restrictor 41 may be provided between the hydrogen source 40 and the valve 20 so as to limit the maximum hydrogen flow rate. Various other components that are numbered similarly in FIG. 2 and FIG. 3 have similar functions and, thus, the descriptions of such components are not repeated in detail here.

Figure 4:
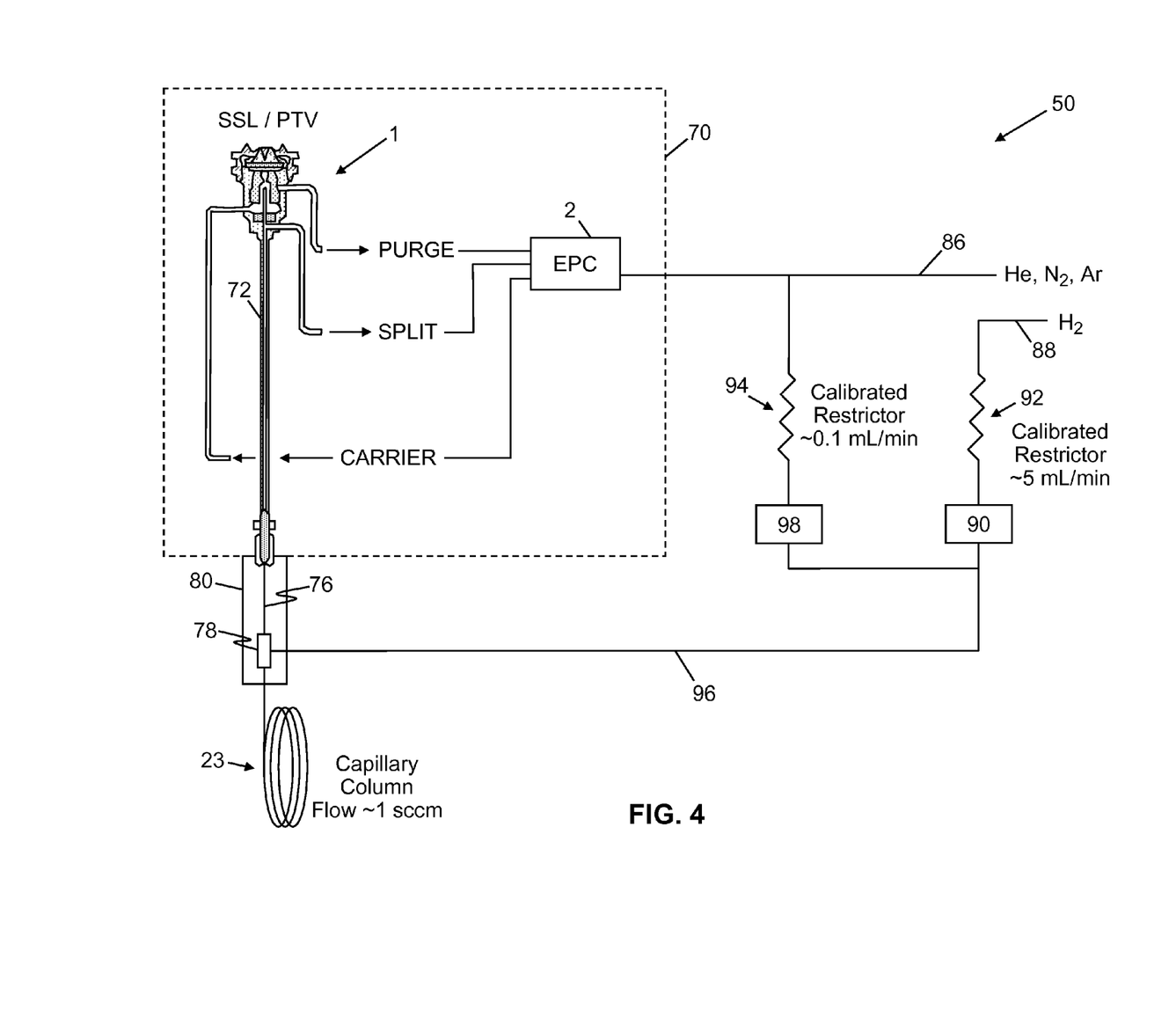
FIG. 4 illustrates a second gas supply and exhaust system for a gas chromatograph in accordance with a second embodiment of the present teachings.

FIG. 4 illustrates a second gas supply and exhaust system 50 for a gas chromatograph in accordance with another embodiment of the present teachings. In the system 50, hydrogen is delivered external to the EPC controller 2 proper. A hydrogen source is delivered into tubing 88 that incorporates a fixed gas-flow restrictor 92. A valve 90 allows blockage of hydrogen transport through restrictor 92. Similarly, an inert gas, such as helium, nitrogen or argon, is delivered into a separate tubing 86 from which it serves to pressurize the EPC unit 2. The inert gas can also serve as a residual gas purge by diverting a portion of the inert gas flow through restrictor 94 (which can be enabled by opening of valve 98). It is preferred to use an inert gas as the residual purge since even low flows of hydrogen, e.g. ~0.1 standard cubic centimeters per minute (sccm), can result in adverse chemical reactions. The purpose of the small residual purge is to prevent back diffusion of solvents and sample into the hydrogen deliver line during sample transfer, and to prevent peak tailing caused by void volume effects. In this non-limiting illustrative example, hydrogen can be delivered at an upper flow of approximately 5 sccm when valve 90 is in the open state, and valve 98 is in the closed state, and a residual purge of approximately 0.1 sccm of inert gas when valve 90 is in the closed state and valve 98 is in the open state. The input pressures of inert gas and hydrogen gas as well as the dimensions of restrictors 92 and 98 can be selected in accordance with the Poiseuille equation such that sufficient hydrogen flow (for prevention of back diffusion of inert gas during analysis) and inert residual gas purge (for prevention of peak tailing) are adequate for the inlet pressure in use. A computer algorithm or look up table can be used to set these pressures according to the analytical column dimensions, flow rates and temperatures of the GC method in use.

A capillary analytical column 23 passes through a tee-piece coupling junction 78, and terminates (i.e., at the column inlet end) within a heated back-diffusion prevention tube 76 whose inner diameter is slightly greater than the outer diameter of the analytical column. The entrance to the column 23 as well as the back diffusion prevention tube 76 and tee piece 78 can be heated within a thermal zone 80 which may be under thermal control that is independent of thermal control of the injection port 72 of injector 1. It is to be understood that the tee piece 78, and back diffusion prevention tube 76 can alternatively be integrated into the lower portion of injection port 72 utilizing the temperature control of the injection port 72 itself rather than thermal zone 80. In this latter case, it is preferable that the entrance to the analytical column 23 terminates within one centimeter of the entrance to the back diffusion prevention tube 76, thereby providing minimum pressure drop and compactness.

In operation of the system 50, either hydrogen or an inert gas passes through the tubing 96 and into the tee piece coupler 78 within which it flows "upward" (more specifically, towards the top of the diagram as shown in FIG. 4) into an annular gap within the tube 76 that surrounds an inlet portion of the analytical column 23. The hydrogen delivered to the tee piece 78 is provided at a flow rate that is somewhat higher than the column flow. For example, 5 mL/min of hydrogen can be delivered for column flows of 1 mL/min. The excess hydrogen will simply be diverted "upwards" (more specifically, towards the top of the diagram as shown in FIG. 4) where it contributes to the bulk purge gas used for septum purge and split flow control. Such back flow of hydrogen also prevents back diffusion of the inert pressurization gas from entering the GC column. Decoupling of the purge gas from the gas used for chromatographic analysis has been described in U.S. Pat. No. 8,371,152 which is incorporated by reference herein in its entirety. The embodiment shown in FIG. 4 allows setting an upper limit to the absolute hydrogen flow to a low level such as 5 sccm. With this arrangement, there will be no unbounded hydrogen flow into the GC oven in the event of a column fracture near the inlet, thereby providing an additional safety factor using hydrogen as a carrier gas. Also, since the absolute flow of hydrogen is low, a single hydrogen generator can serve many gas chromatographs at the same time. When used in conjunction with a nitrogen gas generator, additional safety is provided since no high pressure gas cylinders are needed. Routine changing of high pressure gas cylinders is time consuming, involves safety risks and can contribute to instrument down time during maintenance. Thus, embodiments of the described invention provide a solution for hydrogen use in chromatographs that offer reduced chemical reactions, increased safety and reduced maintenance.

Figure 5:
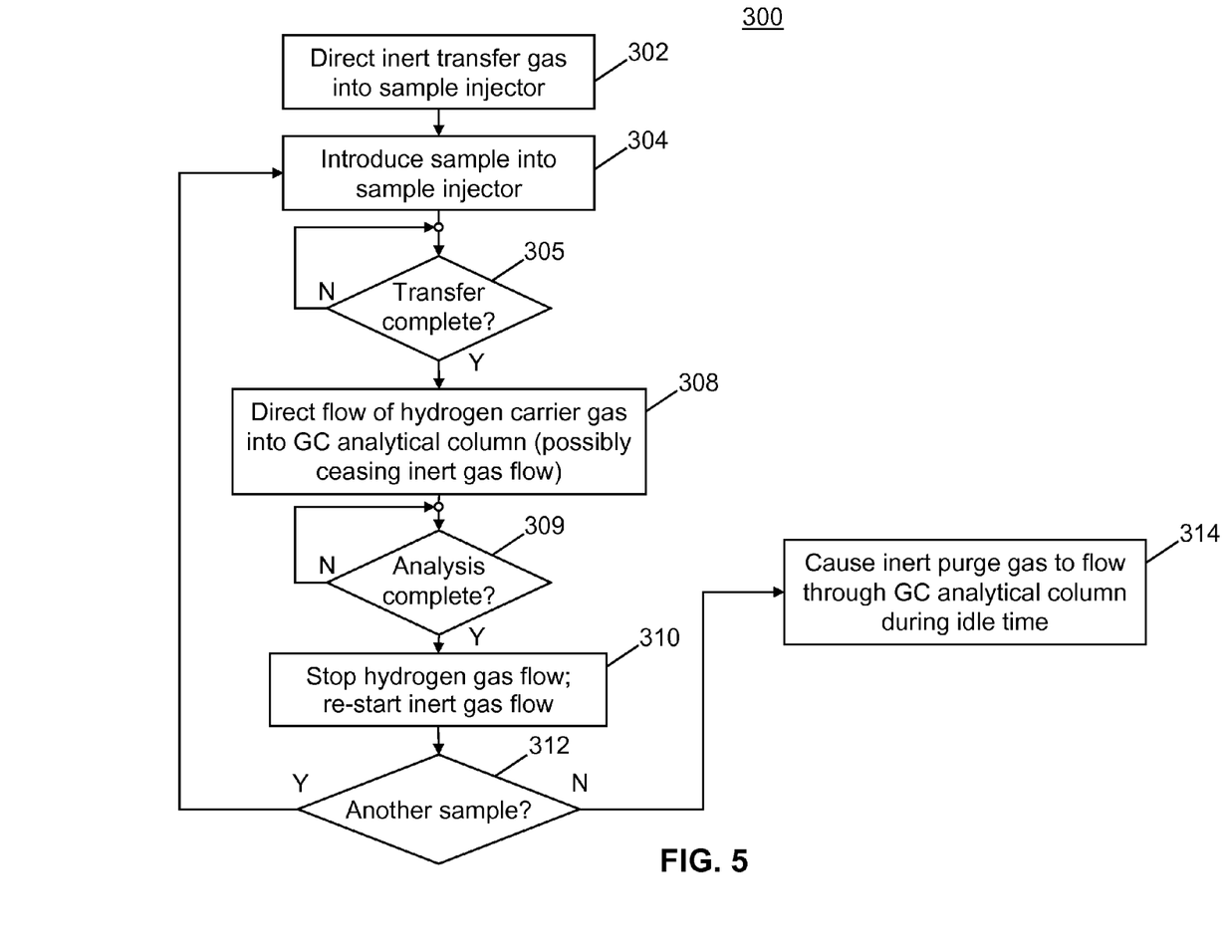
FIG. 5 illustrates a flow diagram outlining a method for operating a gas chromatograph in accordance with an embodiment of the present teachings.

FIG. 5 provides, in flow diagram form, an exemplary method for operating a gas chromatograph system in accordance with the present teachings. Preferably, the method 300 depicted in FIG. 5 is performed by an electronic controller that comprises program instructions to operate electrically coupled fluidic valves and to receive data from electrically coupled gas pressure sensors. In step 302 of the method 300 (FIG. 5), an inert transfer gas, such as helium, nitrogen or argon, is directed into a sample injector of the GC system. The injector may be either a split/splitless or programmed temperature vaporization type. In step 304, a sample is introduced into sample injector while the inert transfer gas is flowing through the injector. As discussed previously, the flow of the transfer gas carries the volatilized sample components to an inlet end of a GC analytical column within which they are focused into a narrow band on the stationary phase. Once this occurs, the transfer to the column is complete (step 305) and a flow of hydrogen carrier gas is directed into and through the GC analytical column (step 308). Step 305 may simply comprise waiting for a predetermined time duration.

As discussed previously the carrier gas (in this case, hydrogen) facilitates separation of chemical components within the column and transfer of the separated components to a detector—these steps comprising an analysis of the sample. The step (308) of directing the hydrogen gas flow into the column may comprise inletting the hydrogen into an inlet port of the sample injector (as in the system 30 illustrated in FIG. 3). In such cases, the step 308 may include cessation of the inert gas flow as would be accomplished, for example, by switching the selection valve 20 so as to permit flow of gas from the hydrogen source 40. Alternatively, the step 308 may comprise inletting the hydrogen into a tee coupler that is fluidically coupled between the sample injector and the GC analytical column, as in the system 50 illustrated in FIG. 4. In such cases, the inert gas may continue to flow through the injector (for septum purge purposes, for example) and an excess of hydrogen gas flow (i.e., a gas flow rate that is greater than can by accommodated by the column) prevents the inert gas from entering into the column.

Once the analysis is complete (step 309) as may be determined by waiting for a given time period, the hydrogen gas flow is stopped and the inert gas flow into the injector is re-started, if necessary (step 310). If another sample is to be analyzed (step 312), then steps 304-310 may be repeated in conjunction with the chromatographic analysis of the other sample. In general, these steps may be repeated any number of times. Once all analyses are complete, the system may enter an idle state in which purge gas is caused to flow through the injector, GC analytical column, or both (step 314). The purge gas may be provided through an inlet port of the injector or may be provided by means of the tee coupler fluidically coupled between the injector and the GC analytical column (FIG. 4).

The discussion included in this application is intended to serve as a basic description. Although the present invention has been described in accordance with the various embodiments shown and described, one of ordinary skill in the art will readily recognize that there could be variations to the embodiments and those variations would be within the scope of the present invention. The reader should be aware that the specific discussion may not explicitly describe all embodiments possible; many alternatives are implicit. Accordingly, many modifications may be made by one of ordinary skill in the art without departing from the scope of the invention. Neither the description nor the terminology is intended to limit the scope of the invention—the invention is defined only by the claims. Any patents, patent publications or other publications mentioned herein are hereby incorporated by reference in their respective entireties.

What is claimed is:

1. A gas chromatography (GC) system comprising:
   a split/splitless sample injector comprising a heater, a gas inlet port a gas outlet port and a split vent port;
   a split vent line fluidically coupled to the split vent port and including a proportional valve;
   a gas inlet line fluidically coupled to the gas inlet port of the split/splitless sample injector;
   a source of inert gas fluidically coupled to the gas inlet line;
   a GC analytical column having an inlet that is fluidically coupled to the gas outlet port of the split/splitless sample injector;
   a tube fluidically coupled between the gas outlet port of the split/splitless sample injector and the inlet of the GC analytical column;
   a source of hydrogen gas;
   a hydrogen supply line having a first end fluidically coupled to the source of hydrogen gas and a second end that outlets the hydrogen gas into the tube through a tee-coupler;
   a calibrated flow restrictor and a first shutoff valve fluidically coupled between a first and a second portion of the hydrogen supply line; and
   an electronic controller electronically coupled to the first shutoff valve,
   wherein the electronic controller comprises program instructions to cause the first shutoff valve to supply a flow of hydrogen carrier gas from the source of hydrogen gas to the GC analytical column through the second portion of the hydrogen supply line and the tube during chromatographic separation of sample components within the GC analytical column and during transport of the separated components to a detector.

2. A GC system as recited in claim 1, wherein the calibrated flow restrictor is configured to limit the flow rate of the hydrogen carrier gas to less than 5 standard cubic centimeters per minute.

3. A GC system as recited in claim 1, further comprising:
   a second shutoff valve and a second calibrated flow restrictor fluidically coupled between the second portion of the hydrogen supply line and the source of inert gas,
   wherein the electronic controller is further electronically coupled to the second shutoff valve and comprises further program instructions to cause the second shutoff valve to supply a flow of purge gas from the source of inert gas to the GC analytical column through the second portion of the hydrogen supply line and through the tube during either a system idle time, a time when a sample is being input to the split/splitless sample injector or a time when a sample is being transferred from the split/splitless injector to the GC analytical column.

4. A GC system as recited in claim 1, wherein the source of hydrogen comprises a hydrogen generator apparatus.

5. A GC system as recited in claim 1, wherein a portion of the GC analytical column including the inlet end thereof protrudes into an interior of the tube such that an annular gap exists between the GC analytical column and the tube.

6. A method for operating a gas chromatography (GC) system comprising a split/splitless sample injector and a GC analytical column, the method comprising:
   (i) introducing a flow of an inert gas into the split/splitless sample injector through a gas inlet port thereof;
   (ii) introducing a liquid sample into a sample port of the split/splitless sample injector such that components of the sample are volatilized therein and transferred from an outlet port of the split/splitless sample injector into an inlet end of the GC analytical column under the flow of the inert gas;
   (iii) causing hydrogen carrier gas to flow into and through the GC analytical column so as to facilitate separation of the transferred sample components within the GC analytical column and so as to transport the separated components to a detector; and
   (iv) ceasing the flow of hydrogen carrier gas into and through the GC analytical column.

7. A method for operating a GC system as recited in claim 6, further comprising:
   repeating the recited steps (i) through (iv),
   wherein another liquid sample is introduced into the sample injector during the repeated step (ii).

8. A method for operating a GC system as recited in claim 6, wherein the step (iii) of causing hydrogen carrier gas to flow into and through the GC analytical column comprises causing the hydrogen carrier gas to flow into and through split/splitless the sample injector and into the inlet end of the GC analytical column from the outlet port of the split/splitless sample injector.

9. A method for operating a GC system as recited in claim 8, wherein the step (iii) of causing hydrogen carrier gas to flow into and through the GC analytical column is performed by reconfiguration of a gas selection valve that is fluidically coupled between the gas inlet port of the split/splitless sample injector and each of a source of inert gas and a source of hydrogen gas.

10. A method for operating a GC system as recited in claim 6, wherein the step (iii) of causing hydrogen carrier gas to flow into and through the GC analytical column is performed by introducing a flow of hydrogen gas into a tube that is fluidically coupled between the outlet port of the split/splitless sample injector and the inlet end of the GC analytical column.

11. A method for operating a GC system as recited in claim 10, further comprising:
   (v) causing the inert gas to flow into and through the GC analytical column by introducing a purge flow of the inert as into the tube and into the inlet end of the GC analytical column.

12. A method for operating a GC system as recited in claim 10, wherein the step (iii) of causing hydrogen carrier gas to flow into and through the GC analytical column comprises introducing the flow of the hydrogen carrier gas into the tube at a flow rate that is greater than a maximum flow rate that can be accommodated by the GC analytical column.

13. A method for operating a GC system as recited in claim 10, wherein a portion of the GC analytical column including the inlet end protrudes into the tube and wherein the flow of hydrogen is caused to pass into the inlet end of the GC analytical column after passing through an annular gap defined between the GC analytical column and the tube.

* * * * *

UNITED STATES PATENT AND TRADEMARK OFFICE
CERTIFICATE OF CORRECTION

PATENT NO. : 9,632,064 B2  
APPLICATION NO. : 14/334282  
DATED : April 25, 2017  
INVENTOR(S) : Edward B. McCauley It is certified that error appears in the above-identified patent and that said Letters Patent is hereby corrected as shown below:

Claim 11, Column 11, Line 16:  
Replace "inert as into the tube"  
With --inert gas into the tube--

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*